(12) United States Patent
Narvekar et al.

(10) Patent No.: US 9,387,136 B2
(45) Date of Patent: Jul. 12, 2016

(54) ABSORBENT ARTICLES WITH CHANNEL AND RELATED METHODS THEREFOR

(75) Inventors: Vishal Narvekar, Mansfield, MA (US); Harish A. Patel, Norfolk, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/602,564

(22) Filed: Sep. 4, 2012

(65) Prior Publication Data

US 2014/0065373 A1 Mar. 6, 2014

(51) Int. Cl.
| | |
|---|---|
| A61F 13/53 | (2006.01) |
| B32B 3/30 | (2006.01) |
| A61F 13/532 | (2006.01) |
| B32B 5/02 | (2006.01) |
| B32B 5/14 | (2006.01) |
| B32B 5/16 | (2006.01) |
| B32B 5/18 | (2006.01) |
| B32B 5/24 | (2006.01) |
| B32B 5/26 | (2006.01) |
| B32B 5/30 | (2006.01) |
| B32B 29/02 | (2006.01) |
| B32B 3/26 | (2006.01) |

(52) U.S. Cl.
CPC .............. *A61F 13/5323* (2013.01); *B32B 3/266* (2013.01); *B32B 3/30* (2013.01); *B32B 5/022* (2013.01); *B32B 5/142* (2013.01); *B32B 5/16* (2013.01); *B32B 5/18* (2013.01); *B32B 5/245* (2013.01); *B32B 5/26* (2013.01); *B32B 5/30* (2013.01); *B32B 29/02* (2013.01); *A61F 2013/53054* (2013.01); *B32B 2262/02* (2013.01); *B32B 2262/067* (2013.01); *B32B 2266/0207* (2013.01); *B32B 2266/0214* (2013.01); *B32B 2266/0278* (2013.01); *B32B 2266/0292* (2013.01); *B32B 2307/726* (2013.01); *B32B 2307/728* (2013.01); *B32B 2307/7265* (2013.01); *Y10T 428/24562* (2015.01)

(58) Field of Classification Search
None
See application file for complete search history.

(56) References Cited

U.S. PATENT DOCUMENTS

| | | | |
|---|---|---|---|
| 3,741,212 A | 6/1973 | Schutte | |
| 4,029,101 A | 6/1977 | Chesky et al. | |
| 4,678,464 A | 7/1987 | Holtman | |
| 4,723,953 A | 2/1988 | Rosenbaum et al. | |
| 4,781,710 A | 11/1988 | Megison et al. | |
| 4,892,535 A | 1/1990 | Bjornberg et al. | |
| 5,891,120 A | 4/1999 | Chmielewski | |
| 6,459,016 B1* | 10/2002 | Rosenfeld et al. | 604/378 |
| 6,495,734 B1 | 12/2002 | Fields et al. | |
| 6,573,422 B1* | 6/2003 | Rosenfeld et al. | 604/368 |
| 7,732,036 B2* | 6/2010 | Etchells | 428/76 |
| 7,850,672 B2 | 12/2010 | Guidotti et al. | |
| 8,134,043 B2 | 3/2012 | Di Girolamo et al. | |
| 8,575,418 B2 | 11/2013 | Gabrielii et al. | |
| 2005/0075617 A1* | 4/2005 | Vartiainen | 604/360 |
| 2005/0096615 A1* | 5/2005 | Kuen | A61F 13/536 604/385.01 |
| 2006/0058750 A1* | 3/2006 | Di Girolamo et al. | 604/378 |
| 2006/0081348 A1* | 4/2006 | Graef | A61F 13/15617 162/141 |

(Continued)

OTHER PUBLICATIONS

International Search Report from corresponding PCT application PCT/US2013/055646 mailed Dec. 11, 2013 (4 pages).

*Primary Examiner* — David Sample
*Assistant Examiner* — Donald M Flores, Jr.

(57) ABSTRACT

An absorbent article includes a fluid pervious top sheet, a fluid impervious bottom sheet, and an absorbent core positioned therebetween. The absorbent core includes a plurality of superabsorbent sections defining a channel therebetween.

21 Claims, 3 Drawing Sheets

(56) References Cited

U.S. PATENT DOCUMENTS

| | | |
|---|---|---|
| 2007/0078422 A1 | 4/2007 | Glaug et al. |
| 2007/0142803 A1 | 6/2007 | Soerens et al. |
| 2007/0219523 A1* | 9/2007 | Bruun et al. ........... 604/385.101 |
| 2007/0282291 A1 | 12/2007 | Cole et al. |
| 2007/0299415 A1 | 12/2007 | Poccia, III et al. |
| 2011/0152813 A1* | 6/2011 | Ellingson ...................... 604/374 |

* cited by examiner

ABSORBENT ARTICLES WITH CHANNEL AND RELATED METHODS THEREFOR

BACKGROUND

1. Technical Field

The present disclosure relates generally to disposable absorbent products or articles. More particularly, the present disclosure relates to an underpad having an absorbent core design and configuration including a channel.

2. Related Art

The absorbent article is employed to collect and/or absorb body fluid discharge, such as, blood, menses, urine, aqueous body fluids, mucus, and cellular debris. Absorbent articles include, for example, disposable diapers, adult incontinent pads, sanitary napkins, party-liners, and the like, that are generally worn in cooperation with garments and disposed against a body surface, by infants and/or adults. Absorbent articles may also be underpads suitable for use with patient bedding, e.g., a disposable underpad placed under a patient.

SUMMARY

The articles disclosed herein provide reduced leakage by utilizing multiple layer top sheet and/or absorbent core arrangements structured to absorb run off and improved absorbency performance by facilitating dispersal of fluid discharge.

An absorbent article in accordance with the present disclosure includes a fluid pervious top sheet, a fluid impervious bottom sheet, and an absorbent core positioned therebetween. The absorbent core is a discontinuous layer including a plurality of spaced superabsorbent sections defining a channel therebetween. The channel may linearly extend along a length of the absorbent core. The channel, in further embodiments, extends along an entire longitudinal and/or transverse length of the absorbent core.

The superabsorbent sections include an inner zone including a first distribution of superabsorbent polymer particles and an outer zone including a second distribution of superabsorbent polymer particles. The first distribution of superabsorbent polymer particles may be greater than the second distribution of superabsorbent polymer particles. The inner zone can include about 70% of the superabsorbent polymer particles and the outer zone includes about 30% of the superabsorbent polymer particles. In some embodiments, the inner and outer zones extend linearly along the longitudinal length of the absorbent core and align with the channel with the inner zone being proximate to the channel. In some other embodiments, the inner zone extends radially around the channel and the outer zone extends radially around the inner zone.

The absorbent article may include additional layers. The absorbent article may include a non-woven strip disposed between the top sheet and the absorbent core, and/or an absorbent layer disposed between the bottom sheet and the absorbent core. The absorbent layer may extend across the entire length and width of absorbent core, while in some embodiments, the absorbent layer may cover only the length and width of a channel formed of the absorbent core. The absorbent layer may include a uniform distribution of fluff fibers therethrough, or alternatively, may include an inner zone including a first distribution of fluff fibers and an outer zone including a second distribution of fluff fibers. The first distribution of fluff fibers may be greater than the second distribution of fluff fibers. The inner zone can include about 60% of the fluff fibers and the outer zone includes about 40% of the fluff fibers.

In accordance with another aspect of the present disclosure, an absorbent article includes a fluid pervious top sheet, a fluid impervious bottom sheet, and an absorbent core positioned therebetween. The absorbent core is a continuous layer fabricated from a superabsorbent material and defines a channel about a center portion thereof. The channel extends from the top sheet to the bottom sheet. The absorbent core may include an inner zone extending around the channel and an outer zone extending around the inner zone. The inner zone can include a higher distribution of the superabsorbent material than the outer zone.

One or more aspects of the disclosure pertain to an absorbent article comprising a fluid pervious top sheet, a fluid impervious bottom sheet, and an absorbent core positioned between the top sheet and the bottom sheet including a plurality of superabsorbent sections defining at least one channel therebetween. In some configurations, at least one channel is dimensioned to extend linearly along a length of the absorbent core. The at least one channel can be dimensioned to extend along a longitudinal length and a transverse length of the absorbent core. The plurality of superabsorbent sections can be arranged to define a grid of channels therebetween. The superabsorbent sections of the absorbent core can comprise superabsorbent polymer particles. At least one of the plurality of superabsorbent sections can define a first zone comprising a first amount of superabsorbent polymer particles and at least another of the plurality of superabsorbent sections defines a second zone comprising a second amount of superabsorbent polymer particles, the first amount of superabsorbent polymer particles greater than the second amount of superabsorbent polymer particles. The first zone can comprise about at least about 70 wt % of superabsorbent polymer particles and less than about 30 wt % fluff fibers. The first zone and the second zone can be dimensioned to extend linearly along a longitudinal length of the absorbent core. The absorbent article can further comprise a layer of an absorbent material disposed between the bottom sheet and the absorbent core. The absorbent layer comprises a matrix of fluff fibers. The at least one channel can have a width of about 0.1 mm to about 10 mm. The at least one channel can comprise a first portion having a first width, a second portion having a second width, and a third portion between the first and second portions, the third portion having a third width greater than the first and second widths. The first width can be about the same as the second width. The plurality of absorbent sections that define the at least one channel therebetween can define a longitudinal channel extending along a length of the absorbent core and at least one transverse channel, each of the at least one transverse channel extending along a width of the absorbent core. The longitudinal channel can be disposed at about the center of the absorbent core and each of the at least one transverse channel is fluidly connected to the longitudinal channel. The absorbent article can further comprise a non-woven strip disposed between the top sheet and the absorbent core.

One or more aspects of the disclosure pertain to a method of fabricating an absorbent article. The method can comprise providing a fluid pervious top sheet, providing a fluid impervious bottom sheet, and positioning an absorbent core between the top sheet and the bottom sheet, the absorbent core comprising a plurality of superabsorbent sections defining at least one channel therebetween. Positioning the absorbent core can comprise providing the plurality of superabsorbent sections comprising a mixture of superabsorbent particles and fluff fiber.

DETAILED DESCRIPTION

Figure 1A:
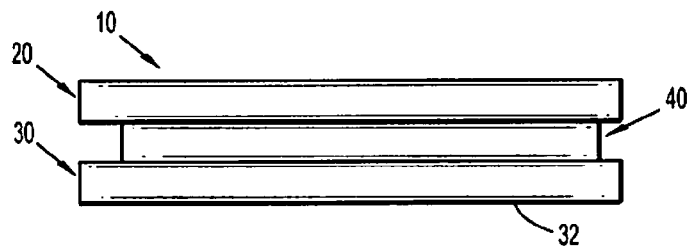
FIG. 1A is a schematic illustration showing a side view of an underpad as an absorbent article or product, in accordance with one or more principles of the present disclosure.

The following discussion includes a description of the presently disclosed absorbent articles in accordance with the principles of the present disclosure. The absorbent article can include a substrate upon and within which fluid discharge, e.g., liquid insult, may be applied and absorbed. For the purposes of discussion, the absorbent article will be discussed in terms of a patient care underpad; however, the presently disclosed absorbent articles may be any absorbent product such as, for example, juvenile diapers and training pants, feminine menstrual pads, adult incontinence products, pet training pads, and other disposable products utilized to absorb fluids. Absorbent articles typically include a three-layer design with a fluid permeable top sheet for engaging the body surface, a fluid impermeable back sheet for preventing fluid leakage through the article, and an absorbent core supported therebetween. The absorbent core usually includes a liquid retention material that faces the body surface. The absorbent core can include loosely formed cellulosic fibers, super-absorbent fibers, super-absorbent particles, or combinations thereof in a continuous or embossed pattern for acquiring and storing fluid discharge. Fluid discharge leakage may result from over-saturation of the absorbent core and/or from pooled fluid run off. For example, during a fluid discharge, urine deposited onto the top sheet may pool before it penetrates the absorbent core. If pooling occurs, urine run off may occur resulting in premature leakage from the absorbent article.

Embodiments of the presently disclosed absorbent article will now be described in detail with reference to the drawings wherein like reference numerals identify similar or identical elements in each of the several views. In the discussion, the term "proximal" or "body side" will refer to the portion of the absorbent article that is closer to a user while the term "distal" or "fixture side" will refer to the portion of the absorbent article that is away from the user. The term "body side" should not be interpreted to necessarily refer to contact with the body of the user, but rather simply means the side that faces toward the body of the user, regardless of whether the absorbent article is actually being used and regardless of whether there are or may be intervening layers between the absorbent article and the body of the user. Likewise, the term "fixture side" should not be interpreted to mean affixed to an article, e.g., garment, bedding, bed, chair, wheelchair, but rather simply means the side that faces away from the body of the user, and therefore towards any fixture which the user is utilizing, regardless of whether there are or may be intervening layers between the absorbent article and the fixture.

Referring now to the figures, wherein like components are designated by like reference numerals throughout the several views, FIG. 1A illustrates a cross-section of a portion of an underpad 10, as an example of an absorbent article in accordance with the present disclosure, including a top sheet 20, a bottom or back sheet 30, and an absorbent core 40 disposed between the top sheet 20 and the bottom sheet 30. The size and shape of the top sheet, bottom sheet, and absorbent core is dictated by the design and usage selected for the absorbent article. Edge portions of bottom sheet 30 may be folded over a portion of the top sheet 20 to form a fluid-tight fold-over edge seal.

Top sheet 20 is a fluid pervious layer for permitting liquid, e.g., menses or urine, to penetrate readily through its thickness. Top sheet 20 may be compliant and/or soft to the touch so that it does not irritate skin. Top sheet 20 may be manufactured from a wide range of materials such as woven and non-woven materials, e.g., a non-woven web of fibers; polymeric materials such as thermoplastic films having apertures, plastic films having apertures, and hydro-formed thermoplastic films; porous foams; reticulated foams; reticulated thermoplastic films; and thermoplastic scrims. Suitable fiber that may be utilized to construct woven and non-woven materials include, for example, natural fibers, e.g., wood or cotton fibers, synthetic fibers, e.g., polymeric fibers such as polyester, polypropylene, or polyethylene fibers, and combinations of natural and synthetic fibers. In embodiments in which the top sheet 20 is a non-woven web, the web may be spun-bonded, carded, wet-laid, melt-blown, hydro-entangled, or formed using any method suitable for forming a non-woven web.

Bottom sheet 30 can be a fluid impervious layer for preventing liquid absorbed and contained in the absorbent core 40 from wetting articles which contact the underpad, such as but not limited to, undergarments, pants, pajamas, and bed sheets. Bottom sheet 30 may be: a woven material; a non-woven material; a liquid-impervious fabric; a cellulosic film; a polymeric film such as a thermoplastic film of polyethylene or polypropylene; an impregnated fluid repellent paper; a composite material, e.g., a polylaminate, such as a film-coated non-woven material; or combinations thereof. Bottom sheet 30, or at least portions thereof, may be embossed or may have matte-finished to provide a cloth-like appearance, and/or colored for ready identification. Bottom sheet 30 may be breathable to allow at least some vapors to escape or pass from the absorbent core 40, while preventing fluid discharge from passing therethrough.

Bottom sheet 30 may be attachable or configured to be attached removably to an article or fixture (not explicitly shown) such as an undergarment or other piece of clothing, a chair, a bed or bedding, a wheelchair or any other suitable fixture in which a patient may require the use of a disposable absorbent underpad. The bottom sheet 30 can include one or more attachment devices (not shown) such as, for example, one or more an adhesive patches or strips, one or more hook-and-loop type connectors, one or more attachment straps, one or more clip connectors, combination thereof, or other suitable connector for retaining the underpad 10 against an article or fixture. Attachment devices (not shown) may be affixed to a fixture side 32 of the bottom sheet 30, and may extended along a portion, or the entire length and/or width of the underpad 10.

Absorbent core 40 typically includes a fluid absorbing material or composition made from exemplary absorbent materials such as but not limited to foams; nonwoven composite fabrics; hydrogels; cellulosic fabrics; super absorbent polymers; woven fabrics; tissue, paper; inherently hydrophilic foams, e.g., viscose rayon foam; natural or synthetic foamed polymeric material, e.g., polyurethane, polyether, or styrene/butadiene rubber foams which have been rendered hydrophilic or readily wettable; comminuted wood pulp; cotton linters and cotton wool of any grade; rayon fibers; cotton staple; bleached or unbleached-creped tissue; and combinations and composites thereof.

The thickness of absorbent core 40 may vary to include thicker and/or thinner areas for optimum performance of the absorbent article.

The absorbent core 40 can include a fibrous matrix of wood fiber or wood pulp fluff. In some embodiments, the absorbent core 40 includes a fibrous matrix of fluff fibers into or onto which superabsorbent polymer (SAP) particles are dispersed. The SAP particles may be continuously or discontinuously distributed through the absorbent core 40 in a uniform manner or in a manner which creates a distribution gradient of SAP particles therethrough.

Figure 1C:
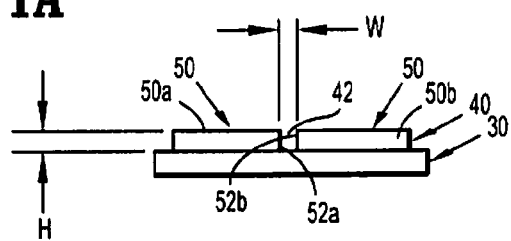
FIG. 1C is a schematic illustration showing a cross-sectional view of the underpad of FIG. 1B.
Figure 1B:
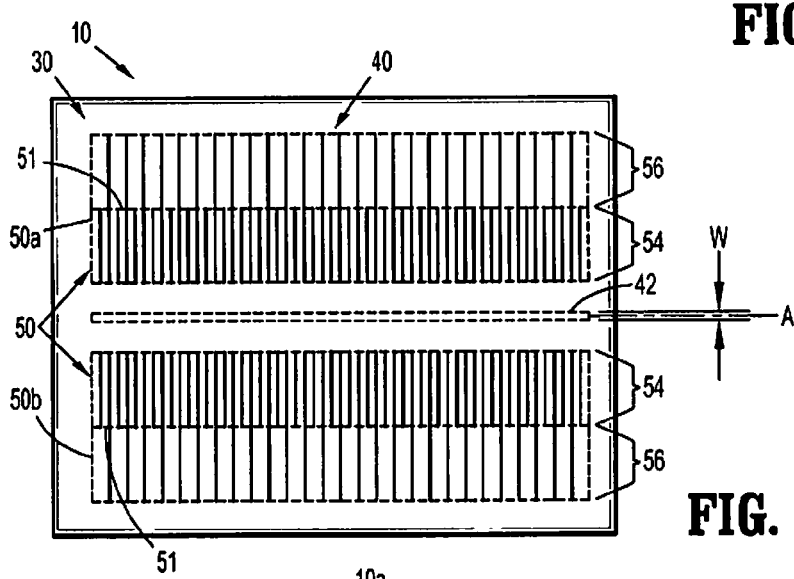
FIG. 1B is a schematic illustration showing a top view of the absorbent core of the underpad of FIG. 1A, in accordance with an embodiment of the present disclosure.

Referring now to FIGS. 1B and 1C, in conjunction with FIG. 1A, absorbent core 40 is exemplarily illustrated as being disposed at about the center of the underpad 10 (shown in relation to bottom sheet 30) and is composed of a plurality of spaced superabsorbent sections 50 defining a channel 42 therebetween. Superabsorbent sections 50 include SAP particles. Channel 42 allows fluid discharge to be absorbed by the aligned superabsorbent sections 50 of the absorbent core 40 while also preventing fluid discharge from flowing outside of the underpad 10. Channel 42 extends along a longitudinal axis "A", e.g., along a machine direction, along the entire length of the absorbent core 40. A first superabsorbent section 50*a* and a second superabsorbent section 50*b* are positioned on opposing sides of channel 42 such that longitudinally extending sides 52*a* and 52*b* define the width "W" of the channel 42. Width "W" of channel 42 may be about 0.1 mm to about 10 mm, and in further embodiments, from about 0.25 mm to about 8 mm, and in some embodiments, from about 1 mm to about 5 mm. Channel 42 also includes a height "H" that extends entirely through the absorbent core 40. Alternatively, the height "H" of the channel 42 may extend through only a portion of the absorbent core 40, as described in further detail below. The width "W" and height "H" of the channel 42 may vary depending upon the application of use of the absorbent article.

The first and second superabsorbent sections 50*a* and 50*b* include an inner zone 54 positioned proximate to the channel 42 including a higher distribution of SAP particles than an outer zone 56. The inner zone 54 of the first and second superabsorbent sections 50*a* and 50*b*, respectively, include at least half, if not a major portion of the SAP particles, relative to the total amount of SAP in the absorbent article . The inner zone 54 can include about 50% to about 90% of the SAP particles, and in some embodiments, about 70% of the SAP particles are distributed in the inner zone 54 of the superabsorbent sections 50.

Figure 1D:
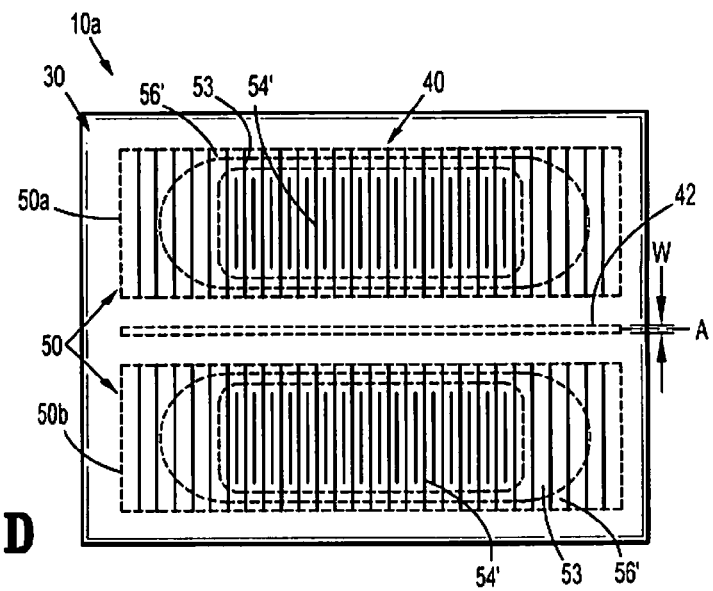
FIG. 1D is a schematic illustration showing a top view of the absorbent core of the underpad of FIG. 1A, in accordance with another embodiment of the present disclosure.

While the inner and outer zones of the first and second superabsorbent sections are illustrated in FIG. 1B as linearly extending along the length of the absorbent core 40, alternatively, as shown in FIG. 1D, the inner zone 54' may be provided in a center portion of the superabsorbent sections 50 while the outer zone 56' is provided around a periphery thereof to form a radial distribution pattern.

An interface 51 (shown in phantom in FIG. 1B) or an interphase 53 (shown in phantom in FIG. 1D) may be present between the inner and outer zones of the superabsorbent sections. The term "interface", as used herein, means a surface forming a boundary between two regions, in this case, for example, between the inner and outer zones. The interface provides a sharp transition or boundary from one zone to another. The term "interphase", as used herein, means the region between the bulk characteristics between the inner and outer zones. An interphase provides a gradual transition or gradient from one zone to another.

In use, the underpad 10 is placed directly under a user such that the center of the underpad 10 is positioned to receive fluid discharge from the user. When the underpad 10 receives fluid discharge, such as an insult of fluid, from the user a majority of the fluid passes through the top sheet 20 and is absorbed by the absorbent core 40. The alignment of the superabsorbent sections 50 and the channel 42, as well as the distribution pattern of the SAP particles within the superabsorbent sections 50, allow for quick migration and/or wicking of the fluid discharge into the absorbent core 40. In addition, the channel 42 may allow for easy folding of the underpad 10 about the center thereof. The underpad is typically discarded after one insult.

Figure 2A:
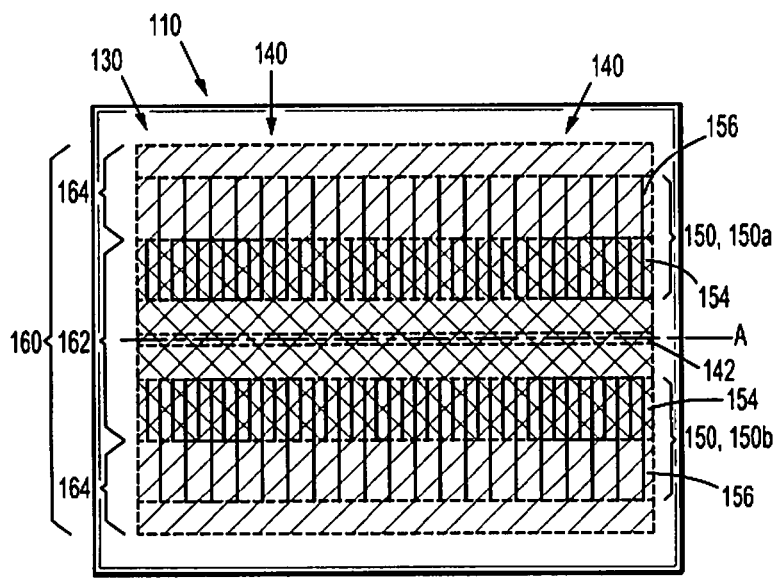
FIG. 2A is a schematic illustration showing a top view of an absorbent core of an underpad as an absorbent article, in accordance with one or more aspects of the present disclosure.
Figure 2B:
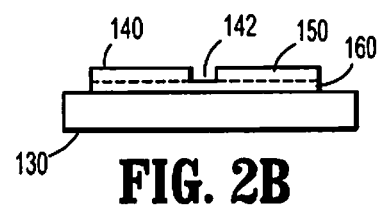
FIG. 2B is a schematic illustration showing a cross-sectional view of the underpad of FIG. 2A.

FIGS. 2A and 2B illustrate another embodiment of an underpad 110 in accordance with the present disclosure. Underpad 110 includes a top sheet (not shown), a bottom sheet 130, and an absorbent core 140 disposed therebetween. The underpad of FIG. 2A is similar to the underpad of FIGS. 1B and 1D, and will be described only with respect to the differences therebetween.

Absorbent core 140 includes an absorbent layer 160 disposed between the superabsorbent sections 150 and the bottom sheet 130. Accordingly, the height "H" of the channel 142 extends only along a portion of the absorbent core, as illustrated in FIG. 2B, along a substantial portion of the absorbent core 140.

Absorbent layer 160 includes a matrix of fluff fibers. An inner zone 162 of the absorbent layer 160 includes a higher distribution of fluff fibers than an outer zone 164. The inner zone 162 can include about 60% of the fluff fibers while the outer zone includes about 40% of the fluff fibers. The inner and outer zones 162 and 164 may be provided in a longitudinal pattern extending along longitudinal axis "A" (as shown) or may be in a radial pattern as described above with respect to the superabsorbent sections of FIG. 1D Like the superabsorbent sections described above, an interface or interphase may be present between the inner and outer zones 162 and 164 of the absorbent layer 160.

Figure 3:
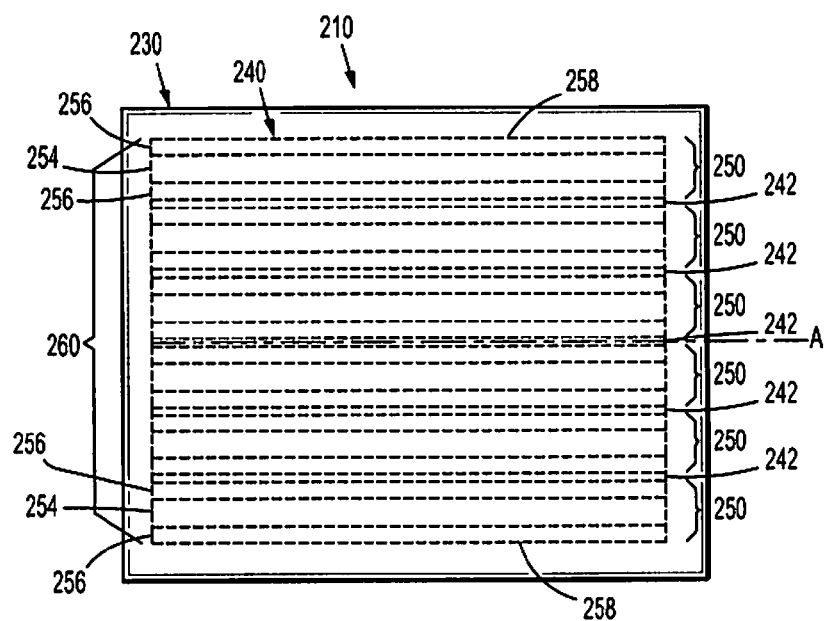
FIGS. 3-6 are schematic illustrations showing top views of an absorbent layer of underpads, in accordance with one or more aspects of the present disclosure.

FIG. 3 illustrates an embodiment of an absorbent article 210 comprising a top sheet (not shown), a bottom sheet 230, and an absorbent core 240 including a plurality of successive superabsorbent sections 250 defining a plurality of channels 242 extending along longitudinal axis "A". Superabsorbent sections 250, and thus channels 242 are arranged or disposed to be parallel or substantially parallel to each other and can be evenly spaced through the absorbent core 240. The spacing between the superabsorbent sections 250 may vary to define channels of varying widths. Superabsorbent sections 250 can each include an inner zone 254 and an outer zone 256, the inner zone 254 including a different, e.g., greater, relative proportion of SAP particles than in the outer zone 256. The inner zone 254 can include about 70% of the SAP particles and the outer zone includes about 30% of the SAP particles. In some embodiments, the SAP particles extend from the inner zone 254 to the outer edges 258 of the outer zones 256 such that the inner zone 254 includes about 70% of the SAP particles, the outer zone 256 includes about 30% of the SAP particles with 10% of the SAP particles being distributed about the outer edges 258.

Figure 4:
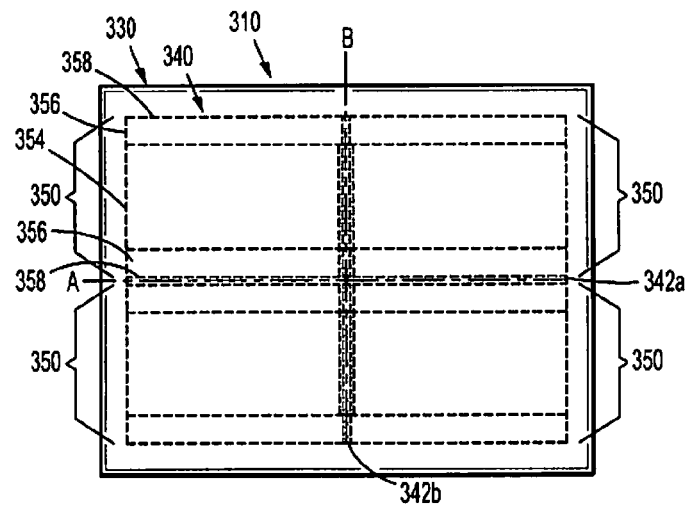

FIG. 4 illustrates an absorbent article 310 comprising an optional top sheet (not shown), a bottom sheet 330, and a plurality of superabsorbent sections 350 successively spaced in a grid-like pattern thereby defining a first channel 342a extending along longitudinal axis "A" and a second channel 342b extending transversely along longitudinal axis "B". The first and second channels 342a and 342b intersect about the center of the absorbent core 340. Superabsorbent sections 350 each include an inner zone 354 including a higher proportion of SAP particles than an outer zone 356. The inner zone 354 can include about 70% SAP particles and the outer zone 356 includes about 30% of the SAP particles. In some embodiments, the SAP particles extend from the inner zone 354 to the outer edges 358 of the outer zones 356 such that the inner zone 354 includes about 70% of the SAP particles, the outer zone 356 includes about 30% of the SAP particles with 10% of the SAP particles being distributed about the outer edges 358.

Figure 5:
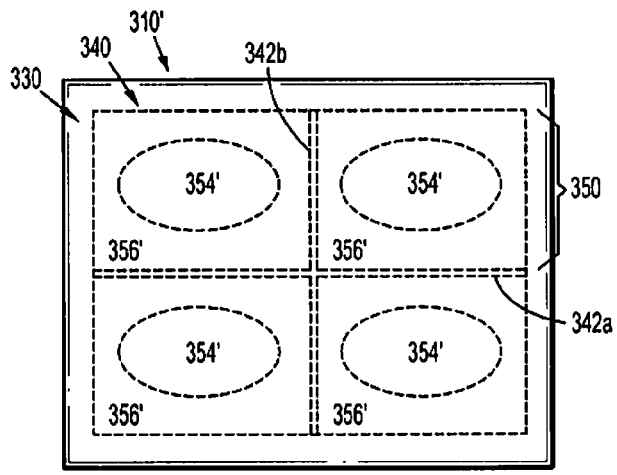

Alternatively, as exemplarily shown in FIG. 5, an absorbent article 310' can have a core 340 with an inner zone 354' at about a center portion of superabsorbent sections 350 while the outer zone 356' may be provided around a periphery thereof to form a radial distribution pattern of the SAP particles.

Figure 6:
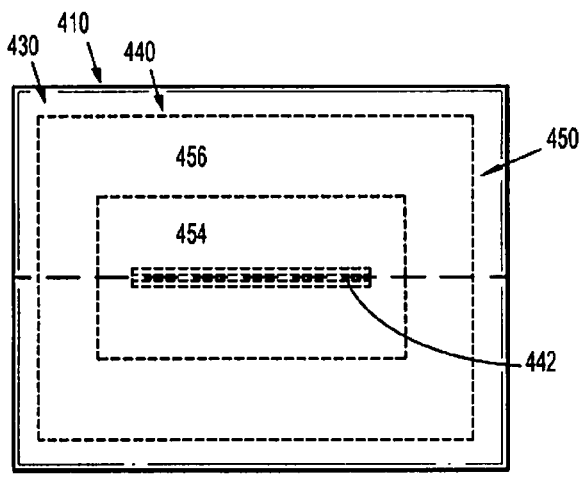

A channel 442 need not extend the entire length of an absorbent core 440, but may be positioned at least partially about a center portion of the absorbent core 440. As illustrated in FIG. 6, channel 442 may be defined within a single superabsorbent section 450 forming the absorbent core, or alternatively, as shown in phantom, two superabsorbent sections may form the channel 442. The superabsorbent section 450 can include an inner zone 454 and an outer zone 456.

The construction may include one or more additional layers such as, for example, an acquisition, intake, or one-way layer configured to manage and/or distribute an inrush of fluid discharge from a user, attachment layers, or other suitable layer including, but not limited to, transfer layers, wicking layers, storage layers, fluid handling layers, rewet barriers, and other layers for enhancing the performance and/or comfort of the absorbent article.

Figure 7:
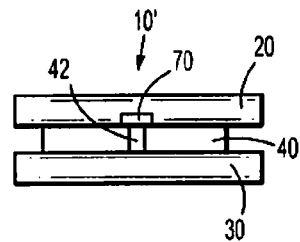
FIGS. 7 and 8 are schematic illustration showing cross-sectional views of underpads, in accordance with one or more aspects of the present disclosure.
Figure 8:
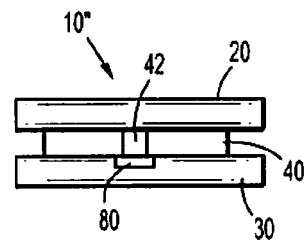

In some embodiments in accordance with one or more aspects of the disclosure, a nonwoven strip 70 may be placed between a top sheet 20 and an absorbent core 40 of an underpad 10' to cover a channel 42 thereby forming a better barrier for migration of any accumulated SAP particles, as illustrated in FIG. 7. A layer of fluff 80 may be applied to the bottom sheet 30 covering the length and width of a channel 42 thus forming a barrier for any migration of fluid discharge out of an underpad 10", as illustrated in FIG. 8. Any additional layers may be fixedly secured by adhesives, such as hot melt, or by other techniques, including for example and without limitation, ultrasonic bonding, heat pressure sealing, and hot air knife bonding.

While the above description contains many specifics, these specifics should not be construed as limitations on the scope of the present disclosure, but merely as exemplifications of embodiments thereof. It is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Those skilled in the art will envision other possible variations that are within the scope and spirit of the present disclosure.

What is claimed is:

1. An absorbent article comprising:
    a fluid pervious top sheet;
    a fluid impervious bottom sheet; and
    a discontinuous absorbent core positioned between the top sheet and the bottom sheet including a plurality of superabsorbent sections defining at least one channel in space between the plurality of superabsorbent sections, the at least one channel linearly extending along a length of the absorbent core and the superabsorbent sections positioned on opposing sides of the at least one channel being in parallel arrangement with respect to each other, and the at least one channel being configured to allow fluid flow in the at least one channel,
    at least one of the plurality of superabsorbent sections defining a first zone comprising a first amount of superabsorbent material and a second zone comprising a second amount of superabsorbent material positioned laterally proximate to the first zone in a transverse direction, the transverse direction being substantially perpendicular to a length of the at least one channel, the first amount of superabsorbent material being greater than the second amount of superabsorbent material, the first and second amounts of superabsorbent material being distributed in a uniform manner through the first and second zones, respectively, and the first and second zones not being separated by a channel of the at least one channel.

2. The absorbent article of claim 1, wherein the at least one channel is dimensioned to linearly extend along an entire longitudinal length of the absorbent core.

3. The absorbent article of claim 2, wherein the at least one channel is dimensioned to extend along the longitudinal length and a transverse length of the absorbent core.

4. The absorbent article of claim 1, wherein the plurality of superabsorbent sections are arranged to define a grid of channels therebetween, the grid of channels including a longitudinal channel extending along a longitudinal length of the absorbent core and a transverse channel extending along a transverse length of the absorbent core, the longitudinal and transverse channels intersecting about a center of the absorbent core.

5. The absorbent article of claim 4, wherein the longitudinal channel is disposed at about the center of the absorbent core.

6. The absorbent article of claim 1, wherein the plurality of superabsorbent sections of the absorbent core comprise superabsorbent polymer particles.

7. The absorbent article of claim 1, wherein the first zone comprises at least about 70 wt % of superabsorbent polymer particles and less than about 30 wt % fluff fibers.

8. The absorbent article of claim 1, wherein the first zone and the second zone are dimensioned to extend linearly along a longitudinal length of the absorbent core.

9. The absorbent article of claim 1, further comprising an absorbent layer disposed between the bottom sheet and the absorbent core.

10. The absorbent article of claim 9, wherein the absorbent layer comprises a matrix of fluff fibers.

11. The absorbent article of claim 1, wherein the at least one channel has a width of about 0.1 mm to about 10 mm.

12. The absorbent article of claim 1, wherein the at least one channel comprises a first portion having a first width, a second portion having a second width, and a third portion between the first and second portions, the third portion having a third width greater than the first and second widths.

13. The absorbent article of claim 12, wherein the first width is about the same as the second width.

14. The absorbent article of claim 1, further comprising a non-woven strip disposed between the top sheet and the absorbent core.

15. The absorbent article of claim 1, wherein the first zone is disposed in a center portion of the at least one superabsorbent section and the second zone is positioned around a periphery thereof.

16. The absorbent article of claim 1, wherein the at least one channel comprises a plurality of channels in parallel and spaced relation.

17. A method of fabricating an absorbent article, comprising:
positioning a discontinuous absorbent core between a fluid pervious top sheet and a fluid impervious bottom sheet, the absorbent core comprising a plurality of superabsorbent sections defining at least one channel in space between the plurality of superabsorbent sections, the at least one channel linearly extending along a length of the absorbent core and the superabsorbent sections positioned on opposing sides of the at least one channel being in parallel arrangement with respect to each other, the at least one channel being configured to allow fluid flow in the at least one channel, at least one of the plurality of superabsorbent sections defining a first zone comprising a first amount of superabsorbent material and a second zone comprising a second amount of superabsorbent material positioned laterally proximate to the first zone in a transverse direction, the transverse direction being substantially perpendicular to a length of the at least one channel, the first amount of superabsorbent material being greater than the second amount of superabsorbent material, the first and second amounts of superabsorbent material being distributed in a uniform manner through the first and second zones, respectively, and the first and second zones not being separated by a channel of the at least one channel.

18. The method of claim 17, wherein positioning the absorbent core comprises providing the plurality of superabsorbent sections comprising a mixture of superabsorbent particles and fluff fiber.

19. An absorbent article comprising:
a fluid pervious top sheet;
a fluid impervious bottom sheet; and
a discontinuous absorbent core positioned between the top sheet and the bottom sheet including a plurality of superabsorbent sections defining at least one channel therebetween, the at least one channel linearly extending along a length of the absorbent core and the superabsorbent sections positioned on opposing sides of the at least one channel being in parallel arrangement with respect to each other, the at least one channel fluidically being configured to allow fluid flow in the at least one channel,
at least one of the plurality of superabsorbent sections defining a first zone comprising a first amount of superabsorbent material and a second zone positioned laterally proximate to the first zone comprising a second amount of superabsorbent material, the first amount of superabsorbent material being greater than the second amount of superabsorbent material, the first and second amounts of superabsorbent material being distributed in a uniform manner through the first and second zones, respectively, wherein the first zone and the second zone are dimensioned to extend linearly along a longitudinal length of the absorbent core and one of the first and second zones is proximate to the at least one channel in a transverse direction, and the other of the first and second zones is laterally spaced from the at least one channel in the transverse direction such that the one of the first and second zones is between the other of the first and second zones and the at least one channel, the transverse direction being substantially perpendicular to the at least one channel, and the first and second zones not being separated by a channel of the at least one channel.

20. An absorbent article comprising:
a fluid pervious top sheet;
a fluid impervious bottom sheet; and
a discontinuous absorbent core positioned between the top sheet and the bottom sheet including a plurality of superabsorbent sections defining at least one channel linearly extending along a length of the absorbent core between the plurality of superabsorbent sections, the at least one channel being configured to allow fluid flow in the at least one channel,
at least one of the plurality of superabsorbent sections defining a first zone comprising a first amount of superabsorbent material and a second zone positioned laterally next to the first zone comprising a second amount of superabsorbent material, the first amount of superabsorbent material being greater than the second amount of superabsorbent material, and one of the first and second zones is proximate to the at least one channel in a transverse direction, the other of the first and second zones is laterally spaced from the at least one channel in the transverse direction, the transverse direction being substantially perpendicular to the at least one channel, and the first and second zones not being separated by a channel of the at least one channel.

21. An absorbent article comprising:
a discontinuous means for absorbing an incident fluid, wherein the discontinuous means comprises a plurality of superabsorbent means for absorbing the incident fluid, at least one superabsorbent means of the plurality of superabsorbent means comprising a first means for absorbing the incident fluid and a second means for absorbing a lesser amount of the incident fluid than the first means for absorbing the incident fluid positioned laterally proximate to the first means for absorbing the incident fluid in a transverse direction, the discontinuous means positioned between a means for allowing the incident fluid to contact the discontinuous means and a means for retaining the incident fluid absorbed by the discontinuous means; and
a means for fluidically distributing the incident fluid along a length of the discontinuous means for absorbing incident fluid, the transverse direction being substantially perpendicular to a length of the means for fluidically distributing the incident fluid, and the first means for absorbing the incident fluid and the second means for absorbing a lesser amount of the incident fluid not being separated by the means for fluidically distributing the incident fluid along the length of the discontinuous means for absorbing incident fluid.

* * * * *